US007033813B2

(12) United States Patent
Castor et al.

(10) Patent No.: US 7,033,813 B2
(45) Date of Patent: Apr. 25, 2006

(54) INACTIVATED VACCINES FOR AIDS AND OTHER INFECTIOUS DISEASES

(76) Inventors: Trevor P Castor, 469 Mystic St., Arlington, MA (US) 02474; Petr O. Ilyinskii, 110 Boston Ave. #1, Somerville, MA (US) 02144; Lisa Lallos, 14 Longmeadow Rd., Chelmsford, MA (US) 01824

( * ) Notice: Subject to any disclaimer, the term of this patent is extended or adjusted under 35 U.S.C. 154(b) by 176 days.

(21) Appl. No.: 10/236,065

(22) Filed: Sep. 5, 2002

(65) Prior Publication Data

US 2003/0108918 A1 Jun. 12, 2003

Related U.S. Application Data

(60) Provisional application No. 60/317,359, filed on Sep. 5, 2001.

(51) Int. Cl.
*C12N 7/06* (2006.01)

(52) U.S. Cl. ....................... 435/238; 435/236; 435/239

(58) Field of Classification Search .................... 435/5, 435/236, 283.1, 298, 238, 289
See application file for complete search history.

(56) References Cited

U.S. PATENT DOCUMENTS

| | | | | |
|---|---|---|---|---|
| 3,887,144 | A | 6/1975 | Schaeffer | |
| 4,466,923 | A | 8/1984 | Friedrich | |
| 4,476,225 | A | 10/1984 | Grigorian et al. | |
| 4,714,591 | A | 12/1987 | Avedesian | |
| RE32,695 | E | 6/1988 | Nahra et al. | |
| 4,749,522 | A | 6/1988 | Kamarei | |
| 5,380,826 | A | 1/1995 | Castor et al. | |
| 5,877,005 | A * | 3/1999 | Castor et al. | 435/238 |
| 6,095,134 | A * | 8/2000 | Sievers et al. | 128/200.14 |
| 6,465,168 | B1 * | 10/2002 | Castor et al. | 435/2 |

FOREIGN PATENT DOCUMENTS

WO WO 93/17724 * 9/1993

OTHER PUBLICATIONS

Fages, J., et al., Viral Inactivation of Human Bone Tissue Using Supercritical Fluid Extraction, ASAIO Journal 1998; 44:289-293.

* cited by examiner

*Primary Examiner*—Jeffrey S. Parkin
(74) *Attorney, Agent, or Firm*—Stephen J. Gaudet

(57) ABSTRACT

Presented herein is a description for the manufacturing of inactivated HIV for use in vaccines against AIDS, as well as other inactivated viruses for other infectious diseases. This invention incorporates methods for inactivating infectious virus particles while retaining protein integrity and antigenicity. The methods utilize critical, near-critical or supercritical fluids with or without polar cosolvents. This invention would allow for the creation of HIV vaccines from genetically attenuated HIV strains for a greater degree of product safety, and from combinations of different HIV strains for broader protection. This HIV vaccine manufacturing technology is inexpensive, amenable to large-scale processing and portable, i.e. it can be readily implemented in a host country site. This invention can be utilized for other viral and bacterial infectious diseases, such as influenza and hepatitis.

13 Claims, 14 Drawing Sheets

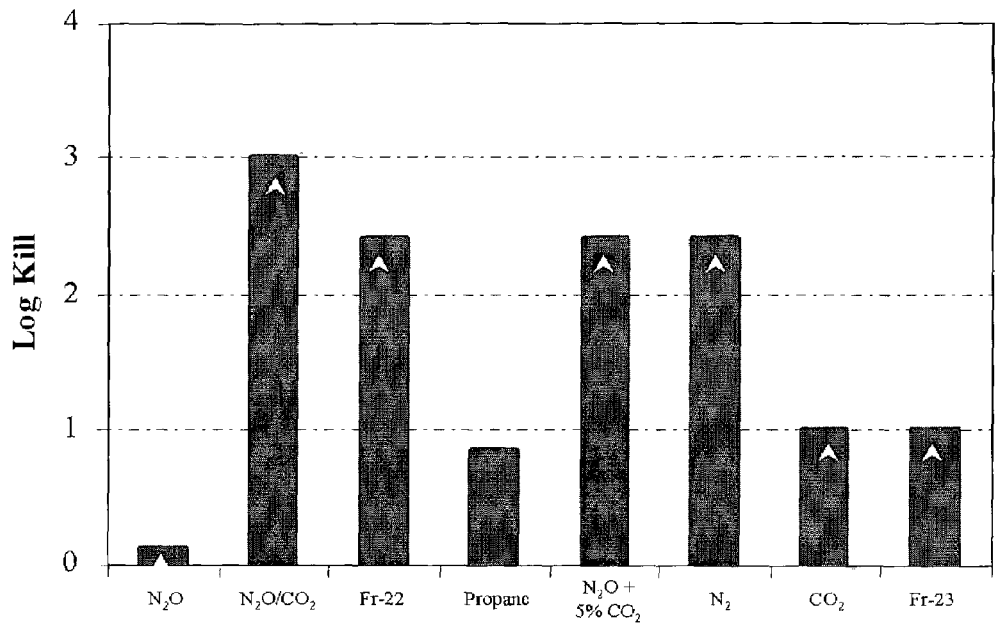

Figure 5: Inactivation of HIV-1 By Different SuperFluids at 3,000 psig and 22°C. Virus-containing supernatant was diluted 1:10 in RPMI and run through the CFI-unit with different SuperFluids conditions. HIV-1 Δ tat-rev was used for each run. An aliquot was not exposed to SuperFluids and served as a time and temperature (t&T) control. 10-fold serial dilutions of the control and treated samples were made and used in the $TCID_{50}$ assay to measure infectious virus. The Log Kill was calculated by dividing the Log $TCID_{50}$/ml of the t&T by the Log $TCID_{50}$/ml of the CFI-Treated sample. $N_2O/CO_2$ - $N_2O$ with trace quantities of $CO_2$, 25 ppm; $N_2O$ + 5% $CO_2$ - a mixture of 95% $N_2O$ and 5% $CO_2$ by volume; White arrows indicate that the Log Kill is greater than the indicated value (Log $TCID_{50}$/ml of the CFI-Treated sample was at the limit of detection).

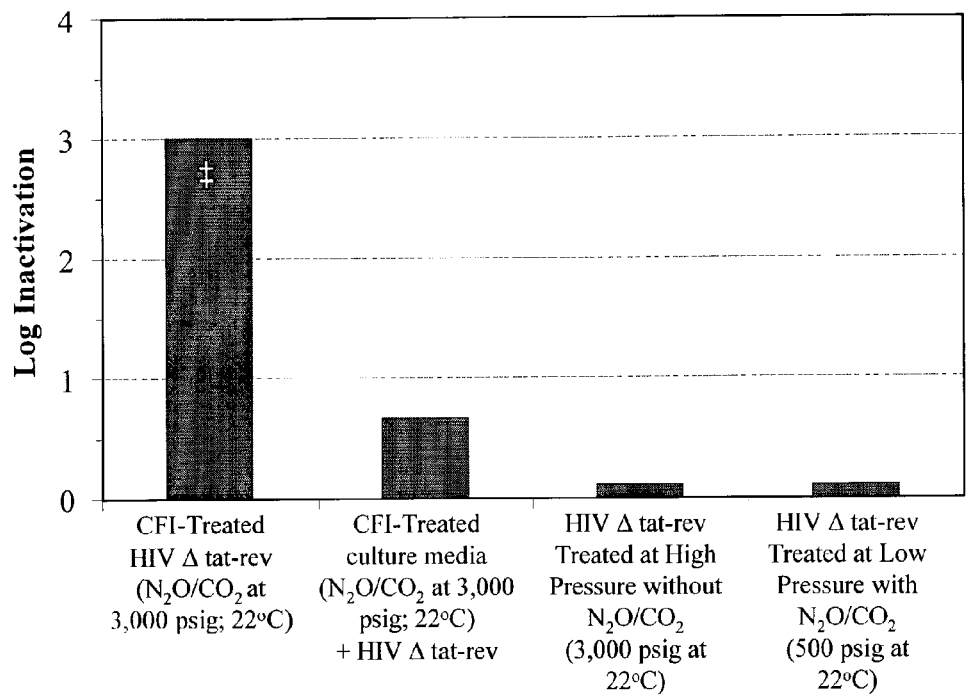
Figure 6: Direct CFI treatment is Necessary and Sufficient to Inactivate HIV-1. $N_2O/CO_2$ - $N_2O$ with trace quantities of $CO_2$; White arrow indicates that the Log Inactivation is greater than the shown value (Log $TCID_{50}$/ml of the CFI-Treated sample was at the limit of detection).

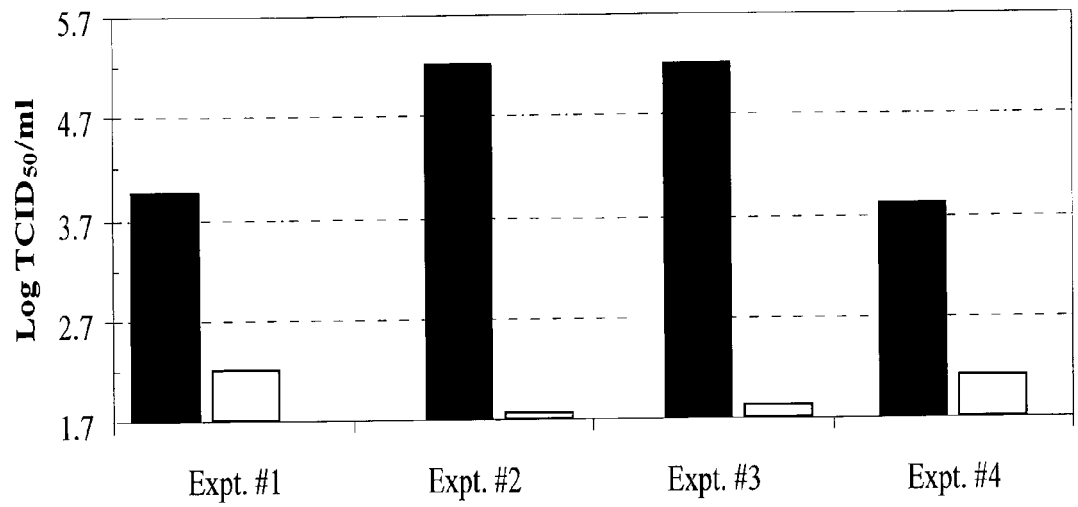

Figure 7: HIV Inactivation by Treatment with SuperFluids $N_2O/CO_2$ at 3,000 psig and 22°C. To determine if the level of inactivation obtained was virus-specific, $HIV_{IIIB}$ was used in Experiment #1. HIVΔtat-rev was used in Experiment #2 and 3 and $HIV_{SF2}$ was used in Experiment #4. Experiment #1 and 4 used virus-containing supernatant, while Experiments #2 and 3 used concentrated virus. Virus was concentrated by centrifuging virus-containing supernatant at 27,000 rpm for 2 hours at 4°C and resuspending the viral pellet in 4 ml of PBS. CFI runs were performed as before except the concentrated virus was diluted 1:2 or 1:4 in RPMI, instead of 1:10. It was noted that cells at the top dilution of virus (1:4) did not grow in experiments #2 and 3, and therefore were not included when calculating the $TCID_{50}$. Thus, the limit of detection for Experiments #2 and 3 is 1.7 logs. Black bars, Control; White bars, CFI-Treated.

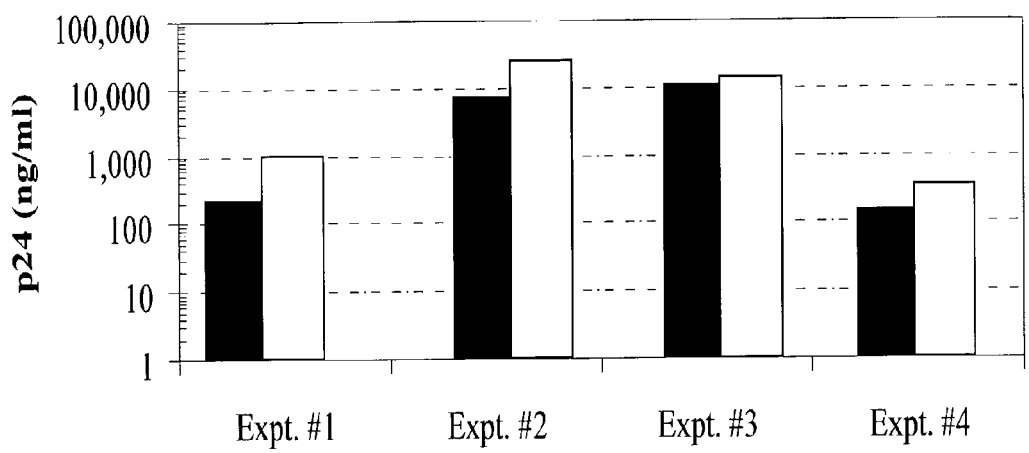

Figure 8: p24 Concentration After Treatment of HIV-1 with SuperFluids $N_2O/CO_2$ at 3,000 psig and 22°C. To determine if the level of inactivation obtained was virus-specific, $HIV_{IIIB}$ was used in Experiment #1. HIV-1Δtat-rev was used in Experiment #2 and 3. Experiment #1 used virus-containing supernatant, while Experiments #2 and 3 used concentrated virus. Virus was concentrated by centrifuging virus-containing supernatant at 27,000 rpm for 2 hours at 4°C and resuspending the viral pellet in 4 ml of PBS. CFI runs were performed as before except the concentrated virus was diluted 1:2 or 1:4 in RPMI, instead of 1:10. Control and Treated samples were analyzed for p24 content by ELISA (SAIC-Frederick). Black bars, Control; White bars, CFI-Treated.

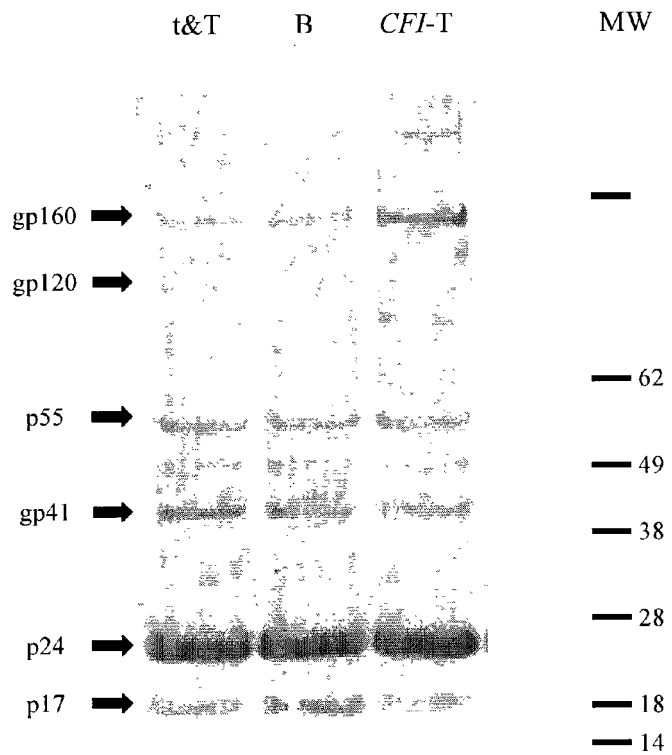

Figure 9: Major HIV Structural Proteins are Present After SuperFluid CFI Treatment. Samples from before the CFI run (lane B), the time and temperature control (lane t&T) and the CFI-treated sample (lane CFI-T) from Experiment #3 were run on a 4-12% Bis-Tris gel, transferred to nitrocellulose and probed with a pool of monoclonal antibodies to HIV (anti-p17, anti-p24, anti-gp120, and anti-gp41) Major HIV proteins are indicated by arrows and bars indicate molecular weight markers.

|        | t&T | B | CFI-T | MW |
|--------|-----|---|-------|-----|
|        |     |   |       | —188 |
| gp120 → | ·•· | ▬▬ | ▬▬ |  |
|        |     |   |       | —62 |
|        | ▬▬ | ▬▬ | ▬▬ |  |
|        |     |   |       | —49 |
|        |     |   |       | —38 |
|        |     |   |       | —28 |
|        |     |   |       | —18 |
|        |     |   |       | —14 |

FIG. 12

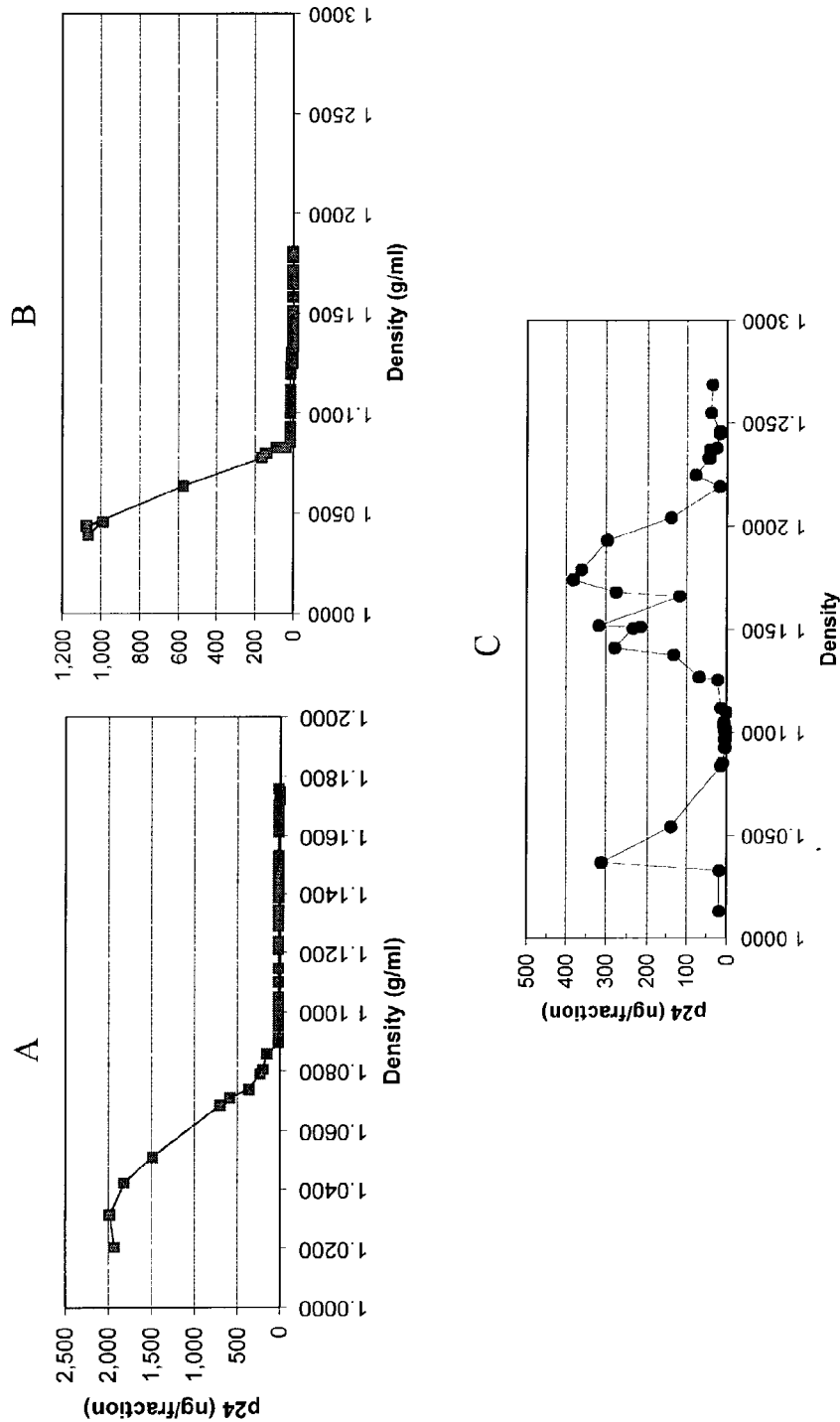

Figure 13: Virion Density is Altered by SuperFluid CFI Treatment. 1 ml of untreated or CFI-treated virus was overlaid onto 20% - 60% sucrose gradient and accelerated at 37,000 rpm for 2.5 hours. Forty 250 µl fractions were collected; the amount of p24 and the density in each fraction was measured. The density of the CFI-treated virus from Experiment #3 (upper left graph) is 1.02 g/ml and that from Experiment #2 (upper right graph) is 1.04 g/ml. The density of untreated virus (lower graph) is 1.17 g/ml, consistent with published reports.

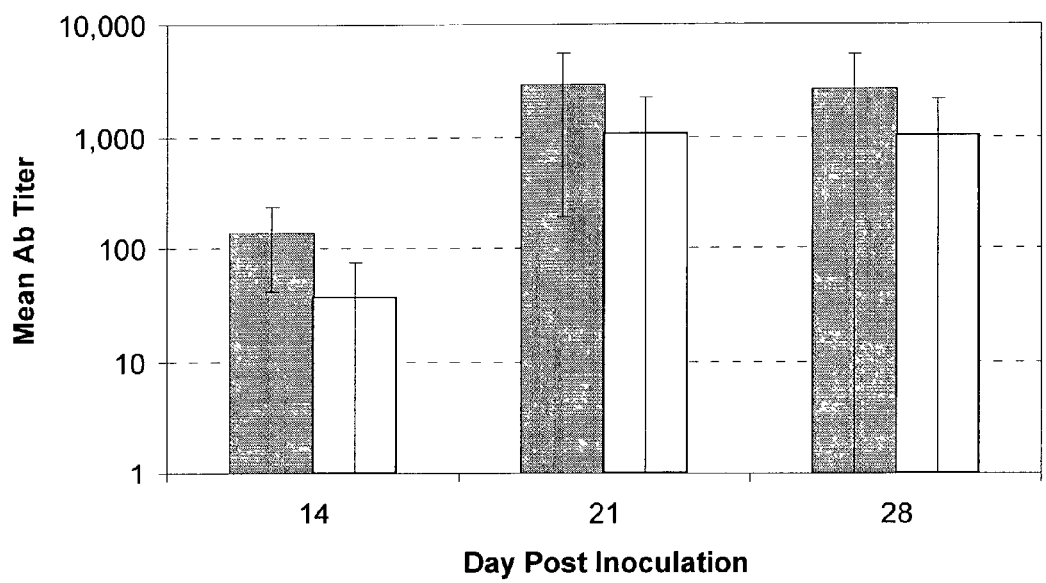
Figure 14: CFI-Treated HIV generates a Humoral Immune Response in Mice. Mice were inoculated with 1.8 μg of p24 of either heat-treated or CFI-treated HIV and the reactivity of antibodies measured against whole lysed HIV over time by ELISA. Gray bars, heat-treated HIV; white bars, CFI-treated HIV. T test, p=0.49.

INACTIVATED VACCINES FOR AIDS AND OTHER INFECTIOUS DISEASES

RELATED APPLICATION

This application claims the benefit of Provisional Application 60/317,359, filed Sep. 5, 2001.

FIELD OF THE INVENTION

This invention relates to inactivated vaccines for AIDS and other infectious diseases. This invention incorporates methods for inactivating infectious virus particles while retaining protein integrity and antigenicity. When introduced into the organism, the inactivated virions will stimulate the human immune response (IR) against the virus, and thus help to establish protective immunity in the vaccinee. The methods also relate to the immunization of animals and livestock. The methods feature critical, near-critical or supercritical fluids with or without polar cosolvents, hereinafter referred to as SuperFluids.

BACKGROUND OF THE INVENTION

Acquired immunodeficiency syndrome (AIDS), identified in 1981, was initially thought to be confined within several risk groups, different from the general population. The isolation of HIV, the infectious agent responsible for AIDS, soon followed and prompted optimistic forecasts regarding the prospects for a future vaccine. These assumptions soon proved unwarranted, since none of the conventional vaccine development strategies was efficient against HIV. At the same time, the disease spread rapidly, affecting millions of people.

Currently, there are 36.1 million AIDS cases worldwide with an estimated 5.3 million new HIV infections during the year 2000. The annual death toll is approximately 2.8 million with the majority of infected individuals in the Third World. There is currently no vaccine against HIV, and AIDS, if untreated, leads to the death of over 95% of infected individuals 10 years post-infection. The only major positive development in the field has been a recent formulation of triple-drug therapy, also called highly active antiretroviral therapy (HAART), in which patients receive a combination of different drugs targeting various viral proteins. Earlier modes of treatment did not contain the virus for long, resulting in the rapid generation of drug-resistant strains and the ultimate progression of the disease. However, while highly successful in many cases, triple-drug therapy is not without caveats.

First, it requires that patients follow the drug regimen thoroughly. Even a short discontinuation of therapy might result in virus re-emergence. Secondly, a patients' quality of life is impaired due to various drug-related side effects. And, most importantly, the cost of these necessary drugs makes them virtually unavailable to the majority of infected individuals, including those outside of health insurance nets of the industrialized world, despite recent political efforts to the contrary. Those efforts, even if they ultimately result in a dramatic slashing of drug prices, may not be able to overturn the tide of the epidemic, since in the foreseeable future, the state of public health systems in the Third World will not permit thorough AIDS diagnostics, drug distribution and monitoring of patients' adherence. Thus, an efficient HIV vaccine will present a major scientific and medical breakthrough. Even if an annual booster is required for protection, such a vaccine will be much more efficient in AIDS prevention than any drug at a reduced cost and with a lower threshold of availability to the general population. This aim of generating a safe and effective HIV vaccine has not yet been reached. In short, the generation of a vaccine against the infectious agent that attacks the immune system itself has proven to be extremely challenging. There are many reasons for this, the main of which is the ingenious way in which HIV replicates and persists in the infected host.

The enormous genetic diversity of HIV presents a major problem for vaccine development. Not only are there numerous viral phenotypes, and new ones are likely to emerge, but also the capability for permanent genetic and antigenic drift enables the virus to evade host immune response (IR) in a single infected person. It is recognized that the immune system of the infected individual mounts a vigorous antiviral response, which contains HIV replication for a prolonged period of time. However, total viral clearance is never reached and accumulating antigenic changes finally enable the virus to avoid the action of the immune system and then, to overcome it. Similarly, HIV is likely to efficiently evade the immune response in an immunized individual if the response generated by the vaccine is too narrow or too weak.

HIV can be genetically categorized into three groups, M, O and N, with M comprising 11 different clades. While one or two clades predominate in various countries, the predominant clade changes over time due to recombination events. Thus, constructing a vaccine that is effective globally is a large undertaking, and possibly not practical. More likely it will be necessary to construct a vaccine effective against one or two clades, and even that may not be useful in the long term. Interestingly, other viruses have been classified based on serotypes, reactivity to immune sera. Classification of HIV based on immunotypes, reactivity to defined monoclonal antibodies is just beginning. Already, though, it has been demonstrated that the genotypes do not correlate with the immunotypes, and that there are fewer immunotypes than genotypes. Constructing vaccines based on immunotypes may thus be a more practical method for obtaining global efficacy for the vaccine.

There is no current theoretical consensus on the necessity of sterile immunity to protect against HIV. Proponents of this requirement point to the capacity of the virus to integrate into the DNA of infected cells and to persist in the organism. Needless to say, this feature of HIV biology provides for another major barrier against successful vaccine development. The opposing viewpoint draws on the above-mentioned capability of an organism to mount a strong anti-HIV IR and on the correlation of disease progression with viral load at the acute stage of infection (set-point). The argument is that the vaccine will already be beneficial if it diminishes viral load at the early stage of infection, thus aiding the immune system of the host. From a practical standpoint, even a partially effective HIV vaccine is thought to provide a positive impact on the AIDS epidemic and therefore sterile immunity is not a prerequisite for products currently being tested and/or developed.

HIV diversity and its capability for antigenic drift are the underlying reasons for the firmly established inefficiency of first-generation HIV vaccines, those that induced a humoral (antibody) response against a limited number of epitopes. Those vaccines used a recombinant envelope protein of HIV, gp120; considerable amount of research has been done using a closely related simian immunodeficiency virus, SIV. It has been recognized that in both cases the bulk of the IR was directed against linear epitopes, while most of the epitopes presented by actively replicating HIV are discontinuous and structure-dependent. The tertiary structure of the virus envelope was not preserved in those first-generation vaccines, having never been attained in genetically engineered gp120 that lacked proper post-translational modification. Furthermore, some of the linear epitopes exhibited high variability among different strains of HIV/SIV and a low level of antigenic cross-reactivity. Consequently, cross-protection in immunized subjects was very low.

A significant problem with an inactivated SIV vaccine was that the protection generated upon live challenge was due to the human cellular antigens present in the envelope. The SIV used as the immunogen was produced in human cells; HIV and SIV incorporate cellular antigens into their envelopes and in this case, SIV incorporated human antigens into its envelope. When macaques were immunized against the inactivated SIV preparation and then challenged with SIV grown in human cells, the macaques were protected. However, when macaques were immunized with either uninfected human cells or with purified human cellular antigens, such as MHC class II, and then challenged with SIV grown in human cells, the macaques were also protected, suggesting that the protective response was due to immunity against the cellular antigens.

Live-attenuated vaccines proved to be extremely efficient in protecting against SIV. However, immunization with live virus results in persistent infection of the vaccinee, which in the case of SIV (and likely HIV) results in an ever-occurring genetic drift and in an emergence of pathogenic viral strains from the original, defective vaccine strain in approximately 10% of animals tested. The weaker live-attenuated mutants, ones that do not replicate efficiently in the organism, seem to be cleared without inducing potent immunity. Collectively taken, this makes the use of a live-attenuated HIV vaccine impractical and unsafe, though efforts are underway to construct a severely defective HIV strain that will replicate in the organism but will not be capable of pathogenic reversion.

The work on the live-attenuated SIV model marked an important scientific breakthrough in the field of HIV vaccines. First, it was shown that protection against an HIV-like virus is possible and, second, that this protection was attained without a marked humoral response in the vaccines. That, together with the failure of inactivated and genetically engineered vaccines, directed the attention of researchers towards strategies capable of generating a vigorous cellular IR against HIV. The accumulated evidence from studying HIV-infected individuals that were able to contain the viral infection further supported this shift. Cellular immune reactions are thought to play a leading role in this containment phenomenon.

There are two main types of recombinant vaccine vectors that generate a strong cellular IR: viral and DNA-based. Of viral vectors, the most advanced in the HIV field are poxviral (using vaccinia or canarypox viruses as a backbone) or adenoviral. Other viral vectors are being actively developed as well. In these settings, recombinant HIV proteins are expressed in the vaccinee using the same transcriptional and translational machinery as the vector genes and a cellular IR results from vector persistence in the organism and its inherent immunogenicity. DNA-based vector is a plasmid containing various HIV protein genes under the control of a strong eukaryotic promoter and other features necessary for efficient transcription and translation of the recombinant gene. Direct inoculation of such a plasmid results in the generation of a cellular IR against the encoded proteins. Both DNA and viral vectors induce a substantial IR in vaccinees, but their protective effects against HIV remain to be demonstrated, although some results obtained on SIV model appear promising. There is no guarantee, however, that any of these approaches will result in a verifiable success in field studies.

The development of inactivated and recombinant protein-based vaccines has, meanwhile, entered a new phase, although there have been lingering doubts on the validity of such approach that mostly results in the generation of humoral immunity. This time, significant attention is being paid to the maintenance of the structure of virion proteins and to the inclusion of different antigenic subtypes. The recombinant protein research avenue has generated the rgp120 product (Vaxgen), which is currently in Phase III trials. The ongoing argument on the efficiency of this product may not be settled by the results of the trial since the FDA will grant a license to manufacturers should the vaccine show at least a 30% efficiency. Such a low immunization threshold standard testifies to the desperate state in which HIV vaccine research finds itself today.

In the last decade, a whole, inactivated HIV vaccine, Remune (The Immune Response Corporation, Carlsbad, Calif.), has been developed as a therapeutic vaccine and entered into clinical trials. Remune is made from a virus that contains clade A envelope and lade G gag proteins, which was inactivated by $\beta$-propiolactone and $^{60}$Co irradiation, and then formulated in incomplete Freund's adjuvant. This inactivated preparation has been shown to be safe and immunogenic. In addition to inducing a humoral response to core proteins, Remune has been shown to induce cross-clade CD4 and CD8 responses, indicating that both arms of the immune system were capable of being stimulated with an inactivated HIV vaccine. Unfortunately, possible due to the lack of gp120 on the Remune vaccine, only a poor therapeutic response was generated as indicated by modest decreases in viral load and small increases in CD4+ T cell counts in HIV-infected patients on HAART.

Recently, it was shown that a number of cysteine-modifying reagents, such as 2,2'-dithiodipyridine (aldrithiol-2; AT-2) render HIV totally non-infective by cross-linking the zinc-fingers of its core protein. This treatment does not result in any structural disruption of HIV virions. HIV and SIV preparations inactivated by this method are currently being tested for their protective capabilities. Thermal and chemical inactivation of HIV is being revisited as well with the aim to minimize irreversible conformational changes in viral proteins. Also, it has been recognized that both arms of the IR, cellular and humoral, need to be stimulated by a successful HIV vaccine and that this may be reached only by using a prime/booster combination of different reagents or vectors, similar to one of the malaria vaccines. Moreover, recent reports show that the generation of neutralizing antibodies is essential for effective natural-killer (NK) cells-directed IR against HIV. Furthermore, there are indications that a strong antiviral humoral response may abrogate AIDS disease in an experimental setting, and that the recombinant HIV immunogen may stimulate considerable cellular response on its own. Taken collectively, this bodes well for the prospects of a multi-component HIV vaccine probably consisting of a vector prime (inducing cellular IR) and inactivated virion or recombinant protein booster (generating humoral IR).

Thus, there are several questions regarding whole inactivated vaccines that remain to be answered including; (1) is protection from challenge due to viral specific immune responses capable of being generated, (2) is cross clade protection capable due to the number of viral proteins present in the whole inactivated vaccine, and (3) can increased survival times, decreased viral loads, and increased CD4+ T cell counts be generated by a therapeutic inactivated HIV vaccine? Inactivated vaccines have several benefits over subunit, live attenuated, DNA or viral vector vaccines including: (1) the immune response may be generated against multiple viral proteins, and (2) easy and inexpensive to produce. Should a whole inactivated vaccine be incorporated into the vaccine regimen, multiple methods of inactivation will need to be employed due to FDA safety requirements. Thus, additional inactivation methods will need to be explored.

The gravity of the epidemiological situation will make any efficient vaccine a highly attractive product, even if it may require an annual boost for maintenance of protection; based on contemporary scientific data, such a scenario is likely. The uses of a whole inactivated vaccine include (1) being part of a vaccine regimen using both DNA or viral vector and a whole inactivated vaccine as the boost for sterilizing immunity; (2) use of the whole inactivated vaccine for therapeutic purposes—especially in cases where HAART has failed and (3) replacement of HAART for the whole inactivated vaccine for use in third world countries that cannot afford the very expensive drugs. The necessary vaccine strategy for HIV may resemble the situation that currently exists with influenza vaccination where annual shots of an inactivated vaccine that targets the predominant viral strain, which differs from year to year, are needed. A whole-killed inactivated HIV vaccine preparation may become a valuable component for such vaccination regimen. Historically, killed HIV vaccines did not exhibit strong immunogenicity and protective efficacy for HIV infection since the thermal or chemical means of inactivation resulted in total or near-total disruption of virion structure, in particular of the denaturation of surface proteins. These concerns are addressed by a novel virus inactivation technology that employs materials known as supercritical, critical or near-critical fluids with or without polar cosolvents or entrainers and their mixtures.

As shown by illustrative example in FIG. 1, a material becomes a critical fluid at conditions that equal its critical temperature and critical pressure. A material becomes a supercritical fluid at conditions that exceed both its critical temperature and critical pressure. The parameters of critical temperature and critical pressure are intrinsic thermodynamic properties of all sufficiently stable pure compounds and mixtures. Carbon dioxide, for example, becomes a supercritical fluid at conditions that exceed its critical temperature of 31.1° C. and its critical pressure of 72.8 atm (1,070 psig). In the supercritical fluid region, normally gaseous substances such as carbon dioxide become dense phase fluids that have been observed to exhibit greatly enhanced solvating power. At a pressure of 204 atm (3,000 psig) and a temperature of 40° C., carbon dioxide has a density of approximately 0.8 g/cc, compared with a density of 0.002 g/cc at standard conditions (0° C. and 1.0 atm), and behaves much like a nonpolar organic solvent, having a dipole moment of zero debyes.

A supercritical fluid displays a wide spectrum of solvation power, as its density is strongly dependent upon temperature and pressure. Temperature changes of tens of degrees or pressure changes by tens of atmospheres can change a compound's solubility in a supercritical fluid by an order of magnitude or more. This feature allows for the fine-tuning of solvation power and the resulting fractionation of mixed solutes. The selectivity of nonpolar supercritical fluid solvents can also be enhanced by addition of compounds known as modifiers (also referred to as entrainers or cosolvents). These modifiers are typically polar organic solvents such as acetone, ethanol, methanol, methylene chloride or ethyl acetate. Varying the proportion of modifier allows wide latitude in the variation of solvent power.

In addition to their unique solubilization characteristics, supercritical fluids possess other physicochemical properties that add to their attractiveness as solvents. They can exhibit liquid-like density yet still retain gas-like properties of high diffusivity and low viscosity. The latter increases mass transfer rates, significantly reducing processing times. Additionally, the ultra-low surface tension of supercritical fluids allows facile penetration into microporous materials, increasing extraction efficiency and overall yields.

A material at conditions that border its supercritical state will have properties that are similar to those of the substance in the supercritical state. These near-critical fluids are also useful for the practice of this invention. For the purposes of this invention, a near-critical fluid is defined as a fluid which is (a) at a temperature between its critical temperature ($T_c$) and 75% of its critical temperature and at a pressure at least 75% of its critical pressure or (b) at a pressure between its critical pressure ($P_c$) and 75% of its critical pressure and at a temperature at least 75% of its critical temperature. In this definition, pressure and temperature are defined on absolute scales, e.g., Kelvin and psia, respectively. Table 1 shows how these requirements relate to some of the fluids relevant to this invention. To simplify the terminology, materials that are utilized under supercritical, near-critical conditions or exactly at their critical point with or without polar entrainers and their mixtures will be jointly referred to as "SuperFluids."

TABLE 1

Physical Properties of SuperFluids

| Fluid | Formula | BP (° C.) | $P_{vap}$ (psia @ 25° C.) | $T_c$ (° C.) | $P_c$ (psia) | 75% of $T_c$ (° C.) | 75% of $P_c$ (psia) |
|---|---|---|---|---|---|---|---|
| Carbon dioxide | $CO_2$ | −78.5 | 860 | 31.1 | 1070 | −45.0 | 803 |
| Nitrous oxide | $N_2O$ | −88.5 | 700 | 36.5 | 1051 | −41.0 | 788 |
| Propane | $C_3H_8$ | −42.1 | 130 | 96.7 | 616 | 4.2 | 462 |
| Ethane | $C_2H_6$ | −88.7 | 570 | 32.3 | 709 | −44.1 | 531 |
| Ethylene | $C_2H_4$ | −103.8 | NA | 9.3 | 731 | −61.4 | 548 |
| Freon 11 | $CCl_3F$ | 23.8 | 15 | 198.1 | 639 | 80.3 | 480 |
| Freon 21 | $CHCl_2F$ | 8.9 | 24 | 178.5 | 750 | 65.6 | 562 |
| Freon 22 | $CHClF_2$ | −40.8 | 140 | 96.1 | 722 | 3.8 | 541 |
| Freon 23 | $CHF_3$ | −82.2 | 630 | 26.1 | 700 | −48.7 | 525 |

BP = Normal boiling point;
$P_{vap}$ = Vapor pressure;
$T_c$ = critical temperature;
$P_c$ = critical pressure SuperFluids, when compressed, exhibit enhanced solvation, penetration and expansive properties. They are utilized to penetrate and inflate viral particles. The overfilled particles are then decompressed and, as a result of rapid phase conversion, rupture at their weakest points. The aim is to introduce minimal controlled damage to the structure of the virion, rendering it non-infective. This will preserve its overall tertiary structure and, possibly, expose some internal epitopes that are usually inaccessible to the immune system.

This technique is purely physical, and does not rely on denaturing heat, chemicals or irradiation.

While previous attempts at developing inactivated vaccines have led largely to disappointment, SuperFluids CFI (critical fluid inactivation) shows great promise as a technique for developing inactivated vaccines that are both safe and protective. Previous inactivated vaccines were unsuccessful due to the degradation of the surface proteins. Techniques used to inactivate HIV have included formalin treatment, detergent disruption, exposure to psoralen and ultraviolet light and treatment with β-propiolactone. Such methods are known to denature protein, chemically modify protein and nucleic acid, disrupt macromolecular interactions and otherwise decrease the ability of the inactivated vaccine to generate an effective IR. In addition, these methods often involve potentially hazardous materials; for example, β-propiolactone is considered carcinogenic. SuperFluids CFI, on the other hand, does not destroy the essential native structure of proteins and can utilize non-carcinogenic or nontoxic substances, such as carbon dioxide or nitrous oxide. Because SuperFluids CFI inactivates enveloped viruses with the potential of retaining the integrity of proteins, this technology presents great promise for the development of an effective whole inactivated vaccine against HIV. Embodiments of the present invention address these problems inherent in the prior art with the application of supercritical, critical or near-critical fluids, with or without polar cosolvents.

SUMMARY

The present invention relates to inactivated HIV and other infectious disease vaccine preparations made through the use of SuperFluids. Embodiments of the present invention are directed to methods of and apparatus for using SuperFluids for making vaccines and vaccine components against AIDS from whole HIV particles. Embodiments of the present invention are also directed to methods of and apparatus for using SuperFluids for making vaccines and vaccine components against other infectious diseases.

The present invention relates to methods and apparatus for inactivating viruses associated with a sample. One embodiment of the present method relates to virus samples, such as HIV and other viruses. The method comprises the steps of forming an admixture of a HIV sample with a critical, near-critical or supercritical fluid, which critical, near-critical or supercritical fluid is capable of penetrating one or more virions associated with the sample. Upon removal of the critical, near-critical or supercritical fluid one or more virions are inactivated. The method further comprises the step of removing the critical, near-critical or supercritical fluid to render one or more virions inactive while retaining the constituents of the virus to form a processed HIV vaccine product. The processed HIV vaccine product exhibits a reduction of viral activity compared with the original HIV sample. The steps of the process can be repeated to effect a desired level of inactivation of virions.

The present method has particular application for the inactivation of HIV virus that is responsible for the blood borne and sexually transmitted disease, AIDS. Surprisingly and unexpectedly, under conditions that leave the HIV virus antigenicity substantially unchanged, more than three logs reduction in viral activity can be achieved in a single-stage or single-pass process. Adding stages or passes to the inactivation process can increase the level of HIV inactivation. For example, the level of inactivation can be increased to more than 6 logs by adding a second stage or pass to the process. As used herein, when referring to HIV vaccine products, the term "substantially unchanged" means exhibiting negligible denaturation of viral surface proteins to no more than fifty percent reduction in the integrity of viral surface proteins. The time in which the HIV virus sample may be processed to achieve this more than three-log reduction in viral activity in a single-stage or single-pass may be as little as five minutes.

Preferably, the critical, near-critical or supercritical fluid is at a temperature in the range of 0° C. to 100° C. This temperature range is in a range in which proteins held in aqueous solutions do not denature. Preferably, the critical, near-critical or supercritical fluid has a temperature that does not exceed 60° C. And even more preferred, the critical, near-critical or supercritical fluid has a range of 4° C. to 40° C.

Preferably, the critical, near-critical or supercritical fluid has a pressure in which the admixture is made and maintained, which pressure is 0.75 to 20.0 times the critical pressure of the gas comprising such fluid.

A preferred fluid is selected from one or more of gases of the group consisting of fluorocarbons, such as chlorofluoromethanes, alkanes, such as ethylene, propane and ethane and binary gases such as nitrous oxide and carbon dioxide and their mixtures. Preferably, the critical, near-critical or supercritical fluid further comprises one or more modifiers selected from the group consisting of ethanol, methanol, acetone and ethylene glycol.

A particular aspect critical, near-critical or supercritical fluid is nitrous oxide with trace quantities of carbon dioxide, in the range of 10 to 1,000 parts per million carbon dioxide at approximately 12° C. to 40° C. and 800 to 5,000 psig; and, even more preferred, nitrous oxide with trace quantities of carbon dioxide, in the range of 10 to 1,000 parts per million carbon dioxide at approximately 16° C. to 26° C. and 1,600 to 5,000 psig; and, most preferred, nitrous oxide with trace quantities of carbon dioxide, in the range of 10 to 1,000 parts per million carbon dioxide at approximately 22° C. and approximately 3,000 psig. At these conditions, more than 3 logs of HIV virus can be inactivated in a single-stage or single-pass processing unit.

A particular aspect critical, near-critical or supercritical fluid is nitrous oxide at approximately 12° C. to 40° C. and 800 to 5,000 psig; and, even more preferred, nitrous oxide at approximately 16° C. to 26° C. and 1,600 to 5,000 psig; and, most preferred, nitrous oxide at approximately 22° C. and approximately 3,000 psig. At these conditions, proteins show little change in function.

A particular aspect critical, near-critical or supercritical fluid is chlorodifluoromethane at approximately 10° C. to 40° C. and 1,000 to 5,000 psig; and, even more preferred, chlorodifluoromethane at approximately 22° C. and 2,000 to 4,000 psig.

One embodiment of the present invention features an apparatus for inactivating one or more virions in an HIV virus sample. The apparatus comprises a vessel for forming an admixture of an HIV virus sample with a critical, near-critical or supercritical fluid, which critical, near-critical or supercritical fluid is capable of being received by one or more virions associated with the sample. Upon removal of the critical, near-critical or supercritical fluid one or more virions are inactivated. The apparatus further comprises depressurization means for removing the critical, near-critical or supercritical fluid to render one or more virions inactive while retaining the constituents of the virus in the sample.

Preferably, the vessel is in communication with a continuous supply of the HIV virus sample. In addition, the depressurization means is capable of receiving a continuous supply of the admixture of the HIV virus sample and the critical, near-critical or supercritical fluid.

Preferably, the vessel retains the admixture for a period of time to effect a thousand-fold to four thousand-fold reduction of active virions. In addition, more preferably, the vessel retains the admixture for a period of one to thirty minutes.

These and other benefits of the present invention will be apparent to individuals skilled in the art upon reading the detailed description and viewing the drawings.

BRIEF DESCRIPTION OF THE DRAWINGS

FIG. 5 in bar graph form illustrates the log reduction of HIV by different SuperFluids at 3,000 psig and 22° C.;

FIG. 6 in bar graph form illustrates that direct CFI treatment is necessary and sufficient to inactivate HIV;

FIG. 7 in bar graph form illustrates that HIV inactivation by treatment with SuperFluids $N_2O/CO_2$ at 3,000 psig and 22° C. is not virus-specific;

FIG. 8 in bar graph form illustrates p24 concentration after SuperFluids CFI-treatment of HIV;

FIG. 9 is a Western blot of control and SuperFluids CFI-Treated samples with an anti-HIV monoclonal antibody pool;

FIG. 12 is a Western blot of control and SuperFluids CFI-Treated samples with an anti-HIV gp120 monoclonal antibody;

FIG. 13 consists of graphs illustrating the density of HIV; two CFI-treated (A and B) and one untreated (C); and FIG. 14 illustrates the generation of HIV-specific antibodies in response to inoculation with either heat-treated or CFI-treated HIV.

DETAILED DESCRIPTION

One embodiment of the present method relates to virus samples. As used herein, virus samples refer to different strains of HIV and other viruses. As used herein, a virion refers to an individual virus particle.

The present invention will be described in detail as a method and apparatus for inactivating one or more virions associated with a virus sample. Individuals skilled in the art will readily recognize the application of the methods and apparatus of the present invention to other purposes. And, individuals skilled in the art will recognize the possibility of changes and modifications to the present apparatus. This description is only exemplary and is not to be interpreted as limiting.

Figure 1:
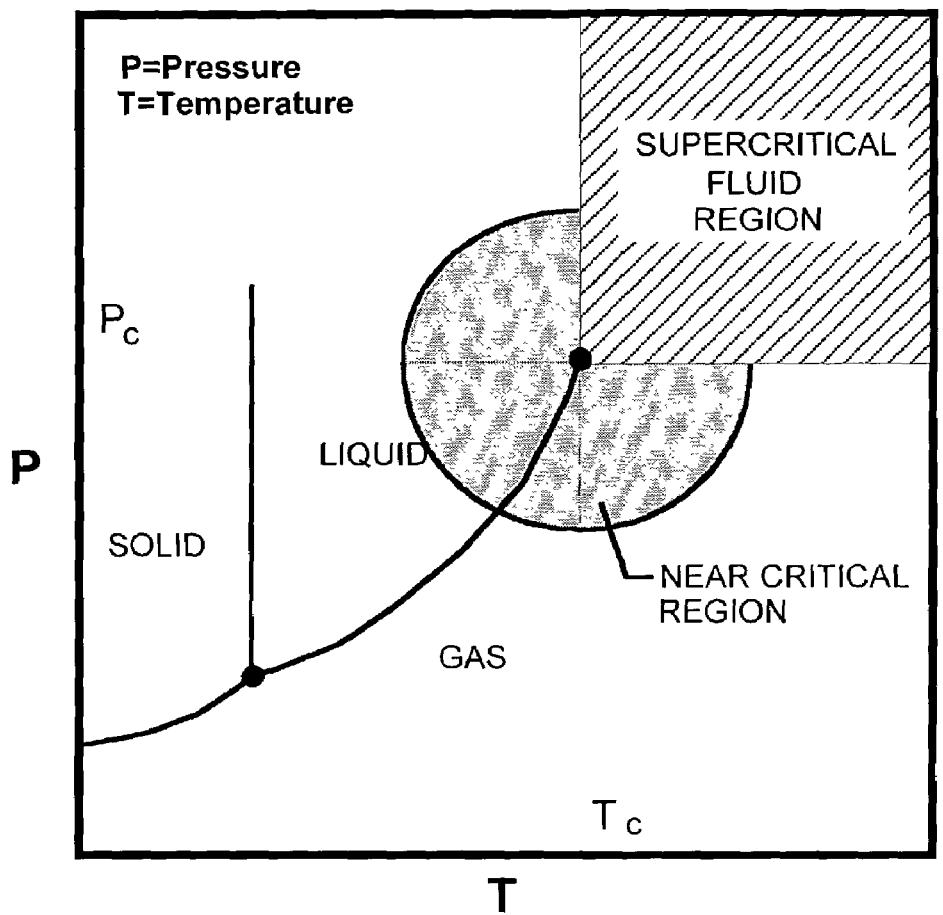
FIG. 1 is a graphical description of the physical states of a fluid under the influence of pressure and temperature.
Figure 2:
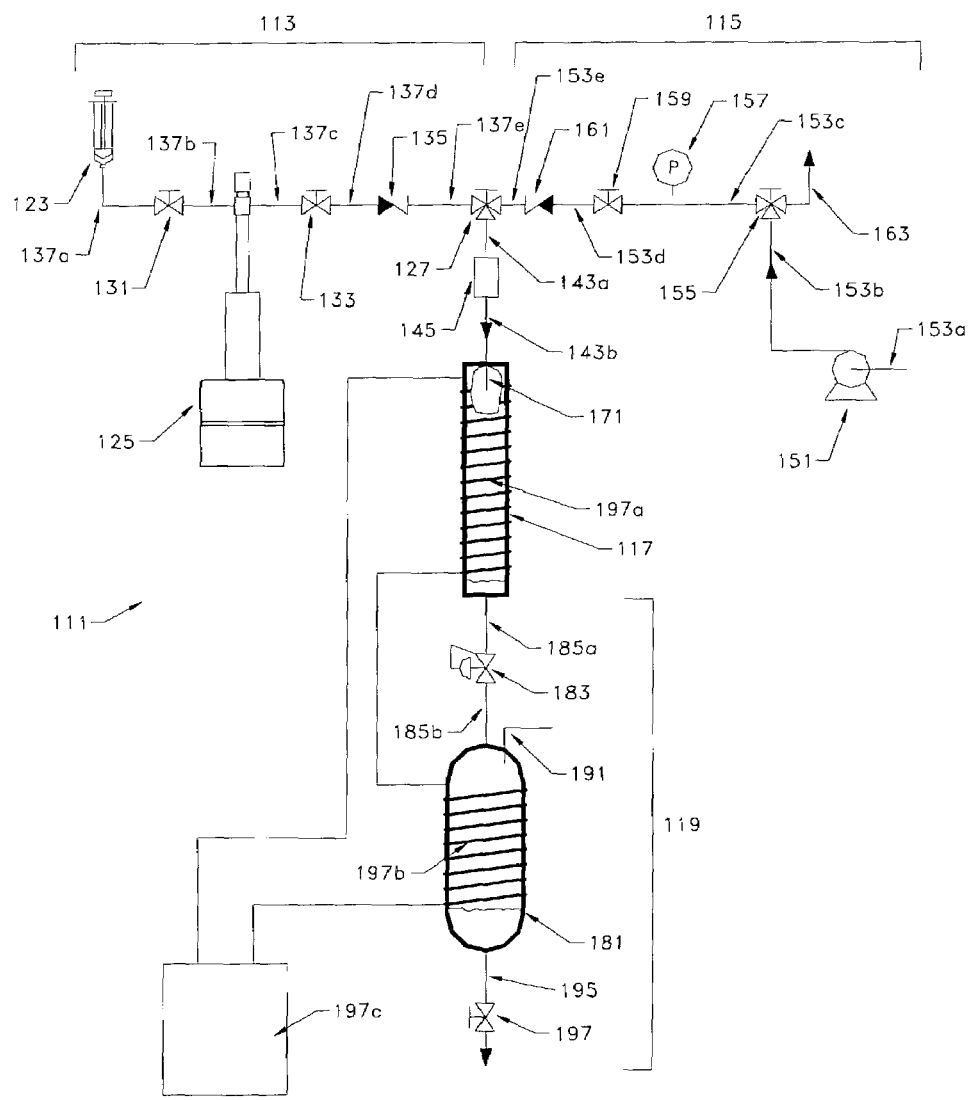
FIG. 2 is a schematic illustration of an apparatus embodying features of the present invention.

An embodiment of the present invention is illustrated in FIG. 2. An apparatus, generally designated by the numeral 111 is depicted. An apparatus 111 is comprised of the following major components, sample injection assembly 113, SuperFluids injection assembly 115, laminar mixing vessel 117 and sample withdrawal assembly 119.

Sample injection assembly 113 receives sample and directs sample into laminar mixing vessel 117. Sample injection assembly 113 comprises sample injection port 123, pump 125, three way valve 127, valves 131 and 133, one-way valve 135 and conduit 137. Sample injection port 123 is in fluid communication with valve 131 via conduit 137a.

Valve 131 is in fluid communication with pump 125 via conduit 137b. Pump 125 is capable of receiving sample from the sample injection port 123 through valve 131. A preferred laboratory scale pump is an Isco Pump 100 DM. Pump 125 is in fluid communication with valve 133 and one-way valve 135 via conduit 137c and conduit 137d, respectively. One-way valve 135 prevents back flow of sample and SuperFluids into the sample injection assembly 113.

One-way valve 135 is in fluid communication with three-way valve 127 via conduit 137e. Three-way valve 127 is capable of receiving sample and directing sample through conduit 143a, filter 145 and conduit 143b into laminar mixing vessel 117.

SuperFluids injection assembly 115 receives SuperFluids from a source [not shown] and directs such fluid to the laminar mixing vessel 117. SuperFluids injection assembly 115 is comprised of pump 151, conduit 153, three-way valve 155, pressure meter 157, valve 159 and one-way valve 161. Pump 151 receives SuperFluids from a source (not shown) via conduit 153a. A preferred pump 151, for laboratory scale, is a Haskel pump. Pump 151 is in fluid communication with three-way valve 155 via conduit 153b. Three-way valve 155 is capable of releasing SuperFluids via vent 163 or directing SuperFluids fluid to valve 159 via conduit 153c. Pressure meter 157 is in communication with conduit 153c to provide pressure readings.

Valve 159 is in fluid communication with one-way valve 161 via conduit 153d. One-way valve 161 prevents the back flow of sample and SuperFluids into the SuperFluids injection assembly 115.

One-way valve 161 is in fluid communication with three-way valve 127. Three-way valve 127 is in communication with laminar mixing vessel 117 via conduit 143a, filter 145 and conduit 143b.

Figures 3, 3A, 3B:
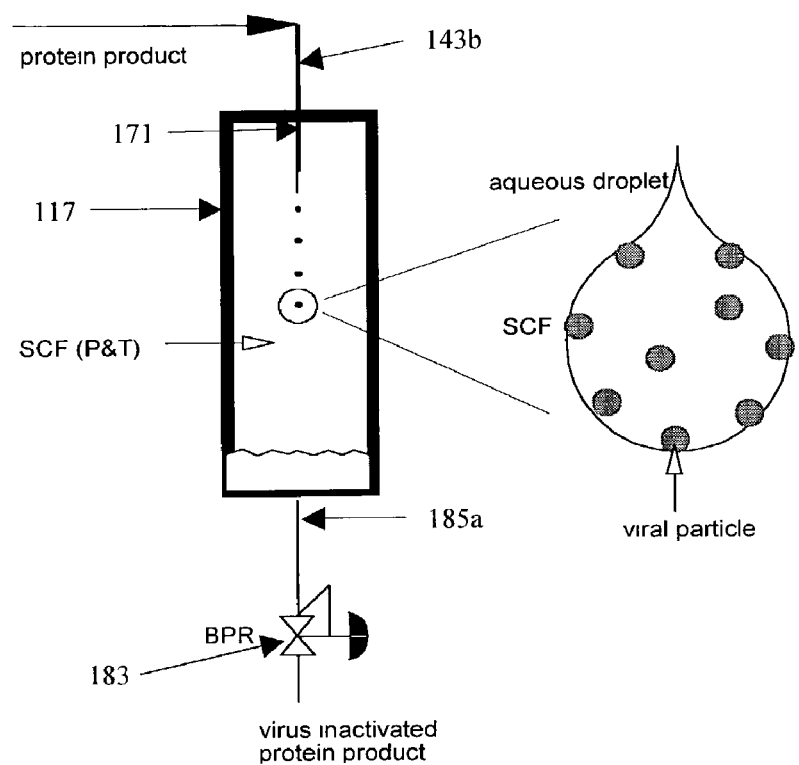
FIG. 3 is a schematic illustration of parts of an apparatus embodying features of the present invention.
FIG. 3A illustrates the laminar mixing vessel.
FIG. 3B illustrates a droplet of sample within such apparatus.

Turning now briefly to FIG. 3A, laminar mixing vessel 117 comprises a closed container in fluid communication with sample injection assembly 113 and SuperFluids injection assembly 115 via conduit 143b. A nozzle 171 extends into the vessel for injecting sample at a controlled rate. Preferably the rate of injection is nonturbulent. For laboratory scale equipment, a 0.005-inch internal diameter tube is preferred. A nozzle 171 of such dimensions is capable of nonturbulent injection of fluid sample up to 10 ml/minute. The sample is injected as a droplet or stream as illustrated in FIG. 3. A fine droplet, as illustrated in FIG. 3B, or stream allows SuperFluids fluid to readily enter the liquid and virus on and/or within the droplet. Virus is depicted as darkened circles in the droplet in FIG. 3B. The droplets or stream preferably have a flow having a Reynolds Number $\leq 2,000$.

Returning now to FIG. 2, the sample and SuperFluids forms a mixture contained in the bottom of laminar mixing vessel 117. Laminar mixing vessel 117 is in fluid communication with sample withdrawal assembly 119.

Sample withdrawal assembly 119 comprises defoaming chamber 181, backpressure regulator 183 and conduit 185. Defoaming chamber is in fluid communication with laminar mixing vessel 117 via conduit 185a and 185b and backpressure regulator 183. Conduit 185a receives samples and SuperFluids mixtures from the bottom of laminar mixing vessel 117.

SuperFluids are released from the sample and SuperFluids mixture in defoaming chamber 181. SuperFluids are removed from defoaming chamber 181 via conduit 191. Conduit 191 is preferably in communication with a flow meter (not shown) and a bleach trap (not shown) to capture and kill any viruses surviving the process. The SuperFluids is vented or recycled.

Sample without SuperFluids collects in defoaming vessel 181 and is removed via a port conduit 195 and valve 197.

The sample can be reintroduced into laminar mixing vessel 171 to obtain further cycles of contact with SuperFluids.

Figure 4:
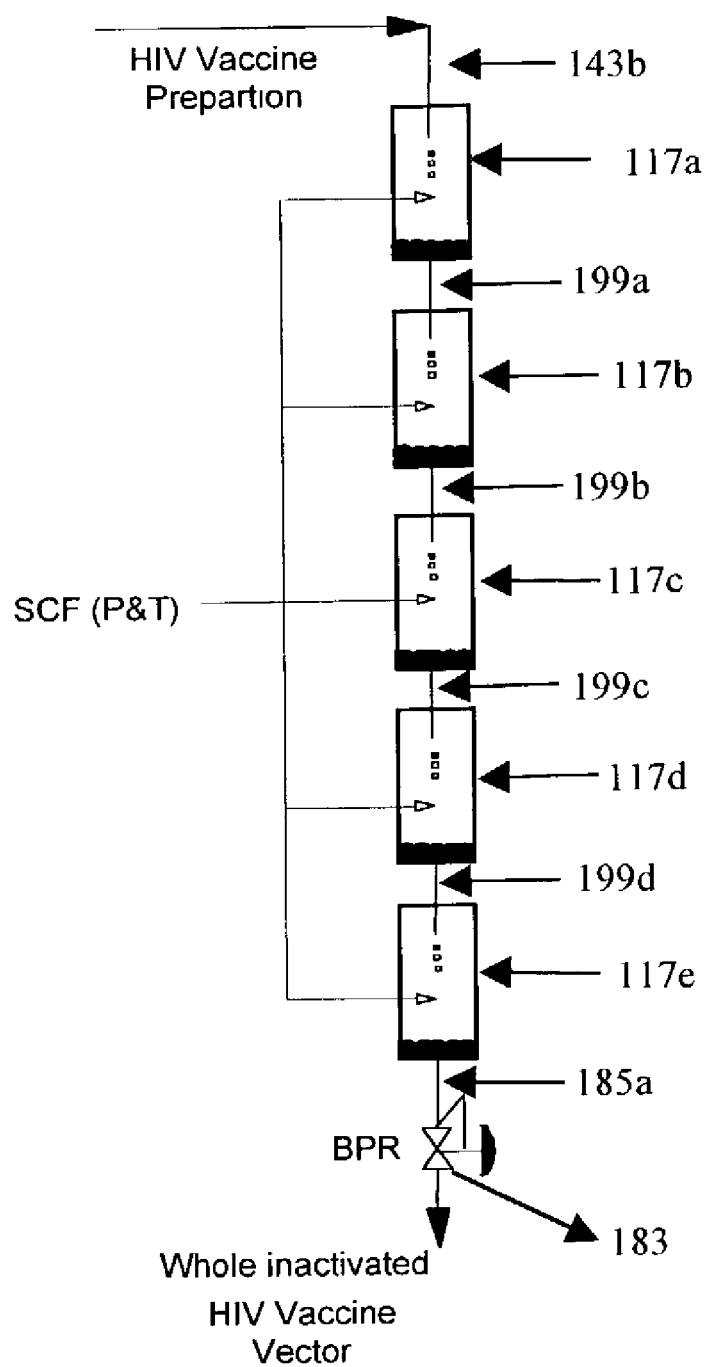
FIG. 4 is a schematic illustration of a multistage apparatus embodying features of the present invention.

In the alternative, as illustrated in FIG. 4, a plurality of laminar mixing vessels 117a–e may be interposed for laminar mixing vessel 117 in apparatus 111. Each laminar mixing vessel 117a–e is in communication with another through suitable conduits 199a–d. The total inactivation of virus in a sample is approximately equal to the inactivation per stage or pass, times the number of passes or stages, plus the final release of pressure.

Preferably, the sample injection assembly 113, SuperFluids injection assembly 115, laminar mixing vessel 117 and sample withdrawal assembly 119 are maintained at a constant temperature by copper tubing jackets 197a and 197b and temperature device 197c control such as a Neslab bath or some alternative method such as a temperature controlled chamber (FIG. 2).

In operation, the SuperFluids injection assembly 115 and laminar mixing vessel 117 are charged with SuperFluids. Three-way valve 127 is placed in communication with sample injection assembly 113 and laminar mixing vessel 117 (FIG. 2). Sample is pumped into Laminar mixing vessel 117 at a constant flow of 0.2 to 4.0 ml/minute. After a few milliliters are received in laminar mixing vessel 117, backpressure regulator 183 is adjusted to release sample and SuperFluids mixtures to the defoaming chamber 181. The mixture is degassed and sample removed through port 195 by opening valve 197.

EXAMPLES

In the examples described herein, HIV MC99IIIBΔtat-rev (herein referred to as HIVΔtat-rev), $HIV_{IIIB}$ and $HIV_{SF2}$ were used. Except where indicated, virus-containing supernatant from day 6 or day 9 postinfection was used. HIVΔtat-rev has the accessory proteins tat and rev deleted. Both of these proteins are essential for HIV replication; therefore, the growth of that strain is possible only in cell lines that express tat and rev proteins in trans, such as the CEM-TART cell line. $HIV_{IIIB}$, the parent virus to HIVΔtat-rev, and $HIV_{SF2}$ were grown in H9 cells. Briefly, $2 \times 10^6$ CEM-TART or H9 cells were incubated for 1 hour at 37° C. with 0.5 ml of HIVΔtat-rev (obtained from the AIDS Repository) or $HIV_{IIIB}$, respectively. After washing the cells twice with 10 ml of growth media, the cells were resuspended in 10 ml growth media and incubated until syncytia were apparent. Harvesting of virus was done by centrifuging the cells at 1200 rpm for 5 minutes, filtering the virus-containing supernatant and making 1 ml aliquots in cryotubes. The virus-containing supernatant was stored at −80° C. and multiple freeze/thaws were kept to a minimum. CEM-TART or H9 cells were resuspended in growth media to continue the infection or discarded to terminate.

Each virus stock was characterized in terms of p24 content and infectivity titer by ELISA or infectivity assay, respectively. Briefly, serial 1:10 dilutions of the virus were made in growth media. These were added to CEM-TART or CEM-SS cells for 1 hour at 37° C. After removal of the virus, growth media was applied to the cells and allowed to incubate at 37° C. for 10–11 days. Every 3–4 days culture media was collected and replaced with fresh media. Collected samples from day 7 were assayed for HIV p24 by ELISA. Wells were scored positive for viral growth if the O.D. was above the cutoff, as determined by the mean plus three standard deviations of the no virus control (n=6). The $TCID_{50}$ was then calculated as per the Spearman-Karber equation that calculates the proportional distance between the dilutions that are above and below 50% (% of wells that contain HIV p24).

Example 1

Inactivation of HIV-1 by Different SuperFluids at 3,000 psig and 22° C.

To determine the effect of different SuperFluids on HIV inactivation, supernatant from HIVΔtat-rev-infected CEM-TART cells was thawed the day of the experiment and diluted 1:10 in RPMI. Diluted virus was used immediately or kept at 4° C. A sample of diluted virus was held at the same temperature for the same time (t&T control) as that applied to the CFI unit. After the run, the tissue culture infectious dose 50 ($TCID_{50}$) assay for the t&T control and CFI-treated samples was begun to measure infectious virus as described above. It was noted that cells at the top dilution of virus (1:10) did not grow, and therefore were not included when calculating the $TCID_{50}$. Thus, the limit of detection for this assay is 2.7 logs. The Log Kill was calculated by dividing the Log $TCID_{50}$/ml of the t&T control by the Log $TCID_{50}$/ml of the CFI-Treated sample.

FIG. 5 and Table 2 show the results of eight experiments using different SuperFluids: $N_2O$, $N_2O/CO_2$ ($N_2O$ with trace quantities of $CO_2$, 23 ppm), Freon-22, Propane, $N_2O+CO_2$ (a mixture of 95% $N_2O$ and 5% $CO_2$ by volume), $N_2$, $CO_2$ and Freon-23. White arrows in FIG. 5 indicate that the Log Kill is greater than the shown value (Log $TCID_{50}$/ml of the CFI-treated sample was at the limit of detection). These results show that greater than 3.4 logs of inactivation can be achieved with SuperFluids $N_2O/CO_2$, while SuperFluids Propane was not able to substantially inactivate HIVΔtat-rev.

TABLE 2

Inactivation of HIV-1 By Different SuperFluids at 3,000 psig and 22° C.
In a Single-Stage Laminar Flow SuperFluids CFI Unit

| Run No. | Super-Fluids | Co-Solvent | Virus | $\text{Log}_{10}$ $\text{TCID}_{50}$/ml (t & T) | $\text{Log}_{10}$ $\text{TCID}_{50}$/ml (CFI-treated) | $-\text{Log}_{10}$ Kill |
|---|---|---|---|---|---|---|
| VAC-5 | $N_2O$ | None | HIV-1Δtat-rev | 2.8 | 2.7 | >0.1 |
| VAC-6 | $N_2O/CO_2$ | None | HIV-1Δtat-rev | 5.7 | 2.7 | >3.0 |
| VAC-8 | Fr-22 | None | HIV-1Δtat-rev | 5.1 | 2.7 | >2.4 |
| VAC-9 | $C_3H_8$ | None | HIV-1Δtat-rev | 5.0 | 4.1 | 0.9 |
| VAC-10 | $N_2O$ | 5% $CO_2$ | HIV-1Δtat-rev | 5.1 | 2.7 | >2.4 |
| VAC-11 | $N_2$ | None | HIV-1Δtat-rev | 5.1 | 2.7 | >2.4 |
| VAC-12 | $CO_2$ | None | HIV-1Δtat-rev | 3.7 | 2.7 | >1.0 |
| VAC-13 | Fr-23 | None | HIV-1Δtat-rev | 3.7 | 2.7 | >1.0 |

Example 2

Effect of Different SuperFluids CFI on HIV-1 p24

To determine the presence of a major capsid protein of HIV after treatment with SuperFluids, the amount of p24 in the t&T control and the CFI-treated samples for each SuperFluid was determined by ELISA (Table 3). Higher amounts of p24 were generally detected in the CFI-treated samples as compared to the t&T control samples.

TABLE 3

Effect of Different SuperFluids at 3,000 psig and 22° C. on HIV-1 p24 In a
Single-Stage Laminar Flow SuperFluids CFI Unit

| Run No. | Super-Fluids | Co-Solvent | Virus | p24 [t & T] (ng/ml) | p24 [CFI-treated] (ng/ml) | Δp24 [% Change] |
|---|---|---|---|---|---|---|
| VAC-5 | $N_2O$ | None | HIV-1Δtat-rev | 56 | 70 | +25 |
| VAC-6 | $N_2O/CO_2$ | None | HIV-1Δtat-rev | 109 | 99 | -9 |
| VAC-8 | Fr-22 | None | HIV-1Δtat-rev | 120 | 112 | -7 |
| VAC-9 | $C_3H_8$ | None | HIV-1Δtat-rev | 146 | 175 | +20 |
| VAC-10 | $N_2O$ | 5% $CO_2$ | HIV-1Δtat-rev | 107 | 82 | -23 |
| VAC-11 | $N_2$ | None | HIV-1Δtat-rev | 107 | 143 | +34 |
| VAC-12 | $CO_2$ | None | HIV-1Δtat-rev | 14 | 15 | +7 |
| VAC-13 | Fr-23 | None | HIV-1Δtat-rev | 14 | 20 | +43 |

Example 3

HIV is Inactivated by CFI and Not by Exposure to CFI-Treated Culture Media

To determine if CFI-treated culture media could inactivate HIV, culture media was treated with SuperFluids $N_2O/CO_2$ (3,000 psig and 22° C.) and used to dilute HIV-1Δtat-rev for the $\text{TCID}_{50}$ assay. This was compared to HIVΔtat-rev that was directly exposed to SuperFluids $N_2O/CO_2$ (3,000 psig and 22° C.). It was noted that cells at the top dilution of virus (1:10) did not grow, and therefore were not included when calculating the $\text{TCID}_{50}$. Thus, the limit of detection for this assay is 2.7 logs. CFI-treated culture media was not able to inactivate HIVΔtat-rev as similar infectivity titers were obtained for control and treated samples, while CFI-treated HIVΔtat-rev was inactivated by greater than 3 logs $\text{TCID}_{50}$/ml (FIG. 6 and Table 4).

To determine if high pressure alone could inactivate HIV, the virus was pressurized to 3,000 psig for 15 minutes (this time exceeds CFI exposure) in the CFI unit and then removed. We also examined whether $N_2O/CO_2$ at a non-supercritical pressure could inactivate HIV by exposing the virus to $N_2O/CO_2$ in the CFI unit at 500 psig. Less than 0.5 log inactivation was obtained in both experiments (FIG. 6 and Table 4). This observation is also supported by data from other investigators, who reported that much higher pressures and residence times are needed to inactivate HIV and SIV by hydrostatic pressure alone.

TABLE 4

Direct CFI Treatment is Necessary and Sufficient to Inactivate HIV-1.

| Treatment Conditions | $\text{Log}_{10}$ $\text{TCID}_{50}$/ml (Control) | $\text{Log}_{10}$ $\text{TCID}_{50}$/ml (Treated) | $-\text{Log}_{10}$ Kill |
|---|---|---|---|
| CFI-Treated HIVΔtat-rev[a] | 5.7 | 2.73 | >3.0 |
| CFI-Treated culture media + HIVΔtat-rev[a] | 4.95 | 5.1 | -0.15 |
| HIVΔtat-rev treated at high pressure without $N_2O/CO_2$[b] | 3.7 | 3.03 | 0.67 |

TABLE 4-continued

Direct CFI Treatment is Necessary and Sufficient to Inactivate HIV-1.

| Treatment Conditions | $\text{Log}_{10}$ $\text{TCID}_{50}/\text{ml}$ (Control) | $\text{Log}_{10}$ $\text{TCID}_{50}/\text{ml}$ (Treated) | $-\text{Log}_{10}$ Kill |
|---|---|---|---|
| HIVΔtat-rev treated at low pressure with $N_2O/CO_2$[c] | 3.06 | 3.34 | −0.28 |

[a]$N_2O/CO_2$, 3,000 psig, 22° C.;
[b]3,000 psig, 22° C.;
[c]$N_2O/CO_2$, 500 psig, 22° C.

Example 4

HIV Inactivation by Treatment with SuperFluids $N_2O/CO_2$ at 3,000 psig and 22° C. is Not Virus-Specific Experiments were conducted to determine if the level of inactivation obtained by SuperFluids CFI was virus-specific. The results of these experiments are plotted in bar graph form in FIG. 7 and the data are presented in Table 5. $\text{HIV}_{IIIB}$ was used in Experiment #1, HIVΔtat-rev was used in Experiments #2 and 3 and $\text{HIV}_{SF2}$ was used in Experiment #4. Experiments #1–3 used a single-stage unit, while Experiment #4 used a two-stage unit. Experiments #1 and 4 used virus-containing supernatant, while Experiments #2 and 3 used concentrated virus. Virus was concentrated by centrifuging virus-containing supernatant at 27,000 rpm for 2 hours at 4° C. and resuspending the viral pellet in 4 ml of PBS. CFI runs were performed as before except the concentrated virus was diluted 1:2 or 1:4 in RPMI, instead of 1:10. It was noted that cells at the top dilution of virus (1:4) did not grow in experiments #2 and 3, and therefore were not included when calculating the $\text{TCID}_{50}$. Thus, the limit of detection for Experiments #2 and 3 is 1.7 logs. SuperFluids CFI treatment inactivated HIVΔtat-rev, $\text{HIV}_{IIIB}$ and $\text{HIV}_{SF2}$.

TABLE 5

HIV Inactivation by Treatment with SuperFluids $N_2O/CO_2$ at 3,000 psig and 22° C. is Not Virus-Specific

| Experiment # | Virus | $\text{Log}_{10}$ $\text{TCID}_{50}/\text{ml}$ (t & T) | $\text{Log}_{10}$ $\text{TCID}_{50/ml}$ (CFI-treated) | $-\text{Log}_{10}$ Kill |
|---|---|---|---|---|
| Experiment #1[a] | $\text{HIV}_{IIIB}$[c] | 3.95 | 2.2 | 1.8 |
| Experiment #2[a] | HIV Δ tat-rev[d] | 5.2 | 1.75 | >3.5 |
| Experiment #3[a] | HIV Δ tat-rev[d] | 5.2 | 1.824 | 3.4 |
| Experiment #4[b] | $\text{HIV}_{SF2}$[c] | 3.82 | 2.1 | 1.72 |

[a]Single stage unit;
[b]two-stage unit;
[c]virus-containing supernatant;
[d]concentrated virus Example 5 p24 Concentration after SuperFluids CFI-Treatment of HIVΔtat-rev, $\text{HIV}_{IIIB}$ or $\text{HIV}_{SF2}$ To determine if a major capsid protein of HIV among different virus strains would be retained after treatment with SuperFluids, the amount of p24 in the t&T control and the CFI-treated samples collected in Example 4, was determined by ELISA. Similar amounts of p24 were obtained with the t&T control and CFI-treated samples for $\text{HIV}_{IIIB}$, HIVΔtat-rev and $\text{HIV}_{SF2}$ (FIG. 8 and Table 6).

TABLE 6 p24 Concentration After SuperFluids CFI-Treatment of HIVΔtat-rev, $\text{HIV}_{IIIB}$ and $\text{HIV}_{SF2}$

| Experiment Number | Virus | p24 [t & T] (ng/ml) | p24 [CFI-treated] (ng/ml) | Δp24 [% Change] |
|---|---|---|---|---|
| Experiment #1[a] | $\text{HIV}_{IIIB}$[c] | 213.8 | 993 | +364 |
| Experiment #2[a] | HIVΔtat-rev[d] | 7,087 | 24,811 | +250.1 |
| Experiment #3[a] | HIVΔtat-rev[d] | 10,288.3 | 13,625 | +32.4 |
| Experiment #4[b] | $\text{HIV}_{SF2}$[c] | 156.1 | 339.7 | +117.6 |

[a]Single stage unit;
[b]two-stage unit;
[c]virus-containing supernatant;
[d]concentrated virus Example 6

Major HIV Structural Proteins are Present After SuperFluids CFI Treatment

Figure 10:
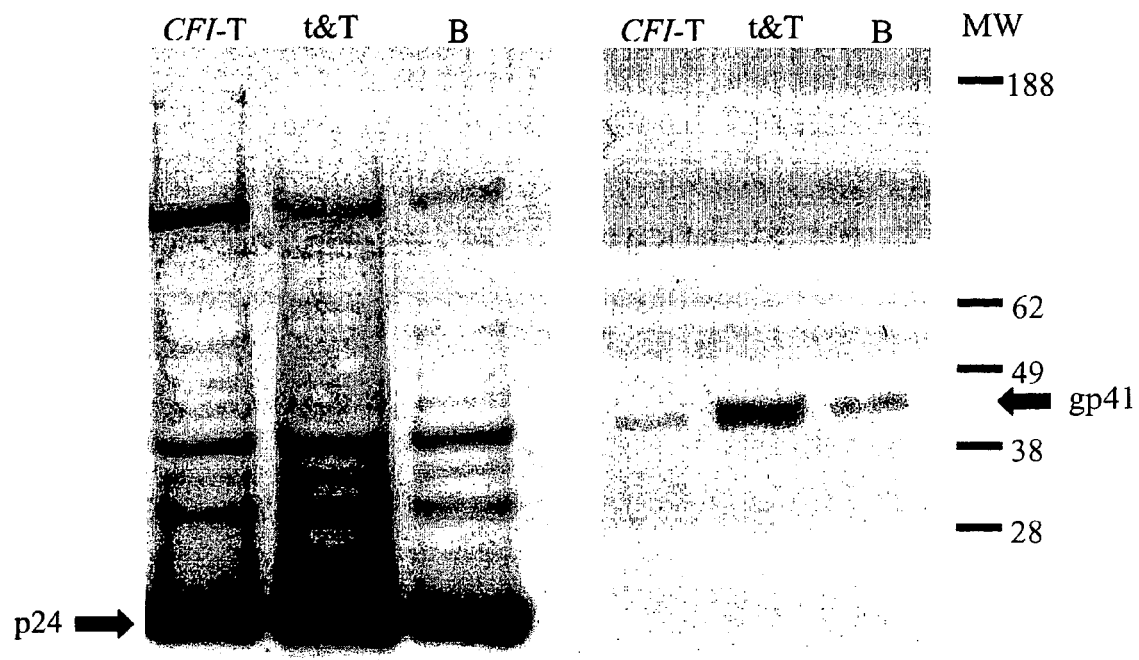
FIG. 10 is a Western blot of control and SuperFluids CFI-Treated samples with anti-HIV p24 and gp41 monoclonal antibodies.
Figure 11:
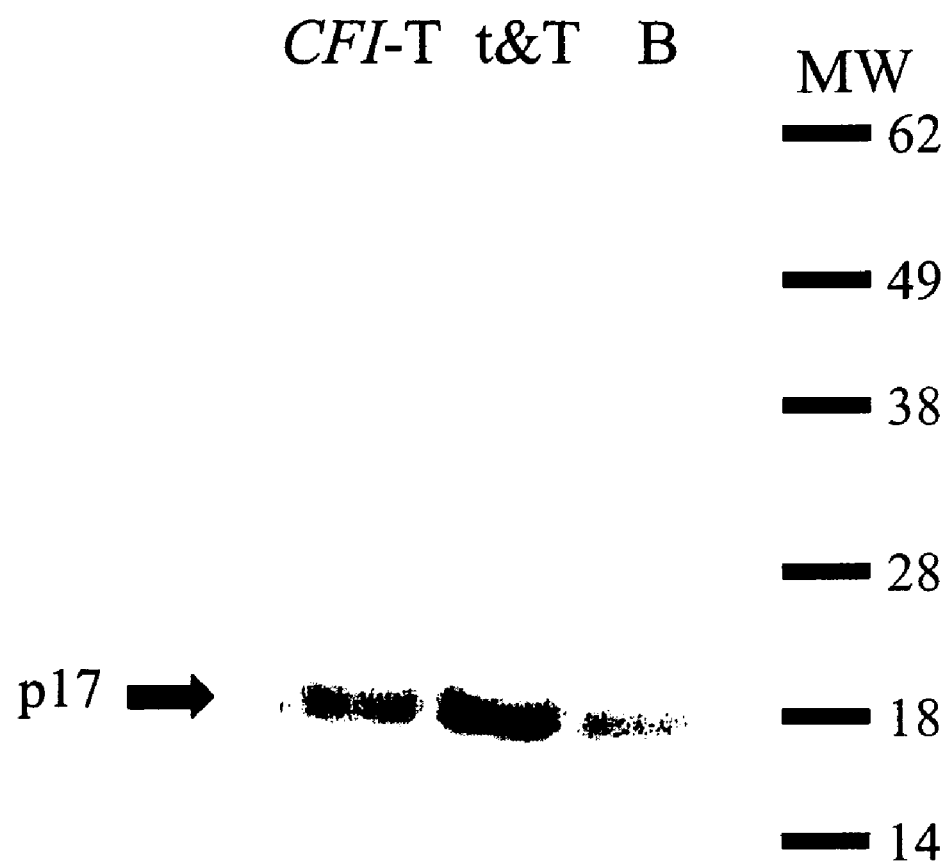
FIG. 11 is a Western blot of control and SuperFluids CFI-Treated samples with an anti-HIV p17 monoclonal antibody.

To assess the presence of several major structural proteins of HIV, a Western blot analysis of control and CFI-treated samples from Experiment #3 in Example 4 was conducted. The monoclonal antibodies used were directed to 4 different HIV proteins: gp120, gp41, p24 and p17. The results of this analysis are presented in FIGS. 9, 10, 11 and 12. Samples from before the CFI run (lane B), the time and temperature control (lane t&T) and the CFI-treated sample (lane CFI-T) were run on a 4–12% Bis-Tris gel, transferred to nitrocellulose and probed with a pool of monoclonal antibodies to HIV (anti-p17, anti-p24, anti-gp120, and anti-gp41; FIG. 9); anti-p24 mAb (FIG. 10, right half) or anti-gp41 mAb (FIG. 10, left half); anti-p17 mAb (FIG. 11); or anti-gp120 mAb (FIG. 12). Arrows indicate major HIV proteins and bars indicate molecular weight markers. These figures show that all four major structural proteins tested are present in the CFI-treated sample, as recognized by monoclonal antibodies, at the same intensity level as the before and t&T controls.

Example 7

CFI-Treated Virions Display an Altered Density as Compared to Untreated Virions

To explore the possibility of a compromised virion structure, the density of CFI-treated virions was determined. Briefly, 1 ml of virus preparation was overlaid onto the sucrose gradient (20%–60%) and centrifuged in an SW40Ti rotor at 37,000 rpm for 2.5 hours. Fractions (250 μl) were collected and the density and p24 of each fraction was measured. HIV has a density range of 1.16 to 1.18 g/ml; a density of 1.17 g/ml was measured for the untreated virus (FIG. 13C). CFI-treated virus from Experiment #2, where complete inactivation was achieved, resulted in a density of 1.04 g/ml, suggesting a compromised structure that may include punctures in the virion (FIG. 13B). A similar density was observed for CFI-treated virions from Experiment #3 where 3.4 logs of virus were inactivated (FIG. 13A).

Example 8

CFI-Treated HIV Generates a Humoral Immune Response in Mice

To determine if CFI-treated HIV could generate a humoral immune response in mice, groups of 5 mice each were injected intraperitoneally (i.p) with either CFI-treated HIV (Experiment #2) or heat-treated HIV (68° C. for 1 hour) in incomplete Freund's adjuvant. Each mouse was injected with 1.8 μg of p24. On days 0, 14, 21 and 28 post inoculation retro orbital bleeds were performed and the sera collected. Antibody titers were measured against a purified HIV lysate in a standard ELISA. Briefly, 500 ng/well of the purified HIV lysate was coated onto wells of a 96-well plate overnight in carbonate buffer (pH=9.6). After blocking the plate with 2% BSA in PBS containing 0.02% Tween 20 (PBST) for 1 hour at 37° C., sera was diluted in PBST and 50 μl/well was added. The plate was incubated at 37° C. for 1 hour. Six half-log dilutions of each serum were tested in duplicate. After washing away unbound sera, the plate was incubated with 50 μl/well of 1:1000 alkaline phosphatase-conjugated goat anti-mouse IgG, IgA, IgM antibody for one hour at 37° C. Substrate was added and the plate incubated at room temperature in the dark for 30 minutes, after which it was read in a microplate reader at 405 nm. Positive (anti-gp41, Chessie 8) and negative controls (normal mouse serum; NMS) were included with each plate. The reciprocal of the highest dilution that gave a positive result, as determined by the mean plus two standard deviations of the negative control, was taken as the antibody titer. In cases where only one replicate was positive, the dilution was considered positive only if the average of the replicates fell above the cutoff.

Results are presented in Table 7 and FIG. 14. The titer of antibodies was similar when mice were inoculated with either heat-treated or CFI-treated HIV (t Test p=0.49). Therefore, CFI-treated HIV is as efficient as heat-treated HIV in generating a humoral immune response.

TABLE 7

Antibody Titer in Sera from Mice Injected I.P. with CFI-Treated and Heat-Treated HIV Particles

| Mouse Number | Day 0 Heat-Treated | Day 0 CFI-Treated | Day 14 Heat-Treated | Day 14 CFI-Treated | Day 21 Heat-Treated | Day 21 CFI-Treated | Day 28 Heat-Treated | Day 28 CFI-Treated |
|---|---|---|---|---|---|---|---|---|
| 1 | — | — | 330 | 33 | 3300 | 330 | 3300 | 3300 |
| 2 | — | — | 100 | 33 | 3300 | 100 | 3300 | 1000 |
| 3 | — | — | 330 | 100 | 100 | 330 | 330 | 3300 |
| 4 | — | — | 100 | — | 1000 | 1000 | 1000 | 100 |
| 5 | — | — | 33 | 33 | 1000 | 1000 | 3300 | 330 |

It is intended that the matter contained in the preceding description be interpreted in an illustrative rather than a limiting sense.

What is claimed is:

1. A method of manufacturing an inactivated virus vaccine product comprising the steps of:
    a) forming an admixture of: a virus sample, wherein said sample contains one or more virions, and a critical, near-critical, or supercritical fluid, wherein said fluid can contain a polar cosolvent;
    b) removing said critical, near-critical, or supercritical fluid to render virions inactive; and
    c) retaining the integrity of one or more viral proteins of said virions to form a processed inactivated virus vaccine product.

2. The method of claim 1, wherein said processed virus vaccine product exhibits a 2.7 log reduction in viral activity compared to said virus sample.

3. The method of claim 1, wherein said critical, near-critical, or supercritical fluid is at a temperature in the range of from 0° C. to 100° C.

4. The method of claim 3, wherein said critical, near-critical, or supercritical fluid has a temperature that does not exceed 60° C.

5. The method of claim 4, wherein said critical, near-critical, or supercritical fluid has a temperature range of 4° C. to 40° C.

6. The method of claim 1, wherein said admixture is formed and maintained at a pressure of 0.75 to 20.0 times the critical pressure of one or more gases comprising the critical, near-critical or supercritical fluid.

7. The method of claim 1, wherein said critical, near-critical or supercritical fluid is selected from one or more of the gases of the group consisting of fluorocarbons, alkanes, binary gases, and a combination thereof.

8. The method of claim 7, wherein said critical, near-critical or supercritical fluid is selected from one or more of the gases of the group consisting of nitrous oxide, chlorodifluoromethane, propane, carbon dioxide, and a combination thereof.

9. The method of claim 1, wherein said critical, near-critical or supercritical fluid comprises one or more of said polar co-solvents selected from the group consisting of ethanol, methanol, acetone, ethylene glycol, and a combination thereof.

10. The method of claim 8, wherein said critical, near-critical, or supercritical fluid is chlorodifluoromethane at approximately 10° C. to 60° C. and 800 to 5,000 psig.

11. The method of claim 8, wherein said critical, near-critical, or supercritical fluid is nitrous oxide at approximately 12° C. to 30° C. and 1,000 to 3,000 psig.

12. The method of claim 8, wherein said critical, near-critical, or supercritical fluid is a mixture of nitrous oxide and carbon dioxide at approximately 12° C. to 30° C. and 1,000 to 3,000 psig.

13. The method of claim 12, wherein said mixture is primarily nitrous oxide with approximately 10 to 1,000 parts per million carbon dioxide.

* * * * *